(12) United States Patent
Pendergast, Jr. et al.

(10) Patent No.: US 10,329,399 B2
(45) Date of Patent: Jun. 25, 2019

(54) PROCESS FOR PURIFICATION OF VENT STREAMS

(71) Applicant: DOW GLOBAL TECHNOLOGIES LLC, Midland, MI (US)

(72) Inventors: John G. Pendergast, Jr., Freeport, TX (US); Johnny W. Masey, Baton Rouge, LA (US); Robert D. Swindoll, Freeport, TX (US); Yujun Liu, Freeport, TX (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 14 days.

(21) Appl. No.: 15/535,801

(22) PCT Filed: Nov. 9, 2015

(86) PCT No.: PCT/US2015/059658
§ 371 (c)(1),
(2) Date: Jun. 14, 2017

(87) PCT Pub. No.: WO2016/099702
PCT Pub. Date: Jun. 23, 2016

(65) Prior Publication Data
US 2017/0335084 A1 Nov. 23, 2017

Related U.S. Application Data

(60) Provisional application No. 62/093,656, filed on Dec. 18, 2014.

(51) Int. Cl.
*B01D 53/14* (2006.01)
*C07C 7/11* (2006.01)
*C08J 11/02* (2006.01)

(52) U.S. Cl.
CPC ......... *C08J 11/02* (2013.01); *B01D 53/1425* (2013.01); *B01D 53/1487* (2013.01);
(Continued)

(58) Field of Classification Search
CPC ..... C07C 7/11; C07C 11/04; B01D 2252/205; B01D 2256/24; B01D 2257/2066;
(Continued)

(56) References Cited

U.S. PATENT DOCUMENTS 8,536,391 B2 * 9/2013 Small .................. C08F 10/14
585/254
2007/0117939 A1 5/2007 Iaccino et al.
2014/0208782 A1 * 7/2014 Joensson ............. F25B 25/02
62/79

FOREIGN PATENT DOCUMENTS

GB      1545885     5/1979
WO   2013154882 A1   10/2013

OTHER PUBLICATIONS

Haynes, W. M. "CRC Handbook of Chemistry and Physics"; 95th Edition, Internet Version (2015); pp. 206, 298, 384, and 386. (Year: 2015).*

(Continued)

*Primary Examiner* — Cabrena Holecek
(74) *Attorney, Agent, or Firm* — Cantor Colburn LLP

(57) ABSTRACT

Disclosed herein is a system for recovering olefins from a vent stream comprising an absorber; and a stripper; where the absorber and the stripper are in a recycle loop; and where the absorber is operative to treat a vent stream with a solvent to remove more than 99 wt % of a halogenated by-product contained in the vent stream and to recover 90 to 95 wt % of olefin molecules present in the vent stream; and where the stripper is operative to remove more than 99 wt % of the (Continued)

halogenated by-products present in the solvent; and where the solvent is recycled to the absorber.

7 Claims, 1 Drawing Sheet

(52) U.S. Cl.
CPC ............ *B01D 53/1493* (2013.01); *C07C 7/11* (2013.01); *B01D 2252/205* (2013.01); *B01D 2256/24* (2013.01); *B01D 2257/2066* (2013.01); *Y02P 20/154* (2015.11)

(58) Field of Classification Search
CPC ............ B01D 53/1425; B01D 53/1487; B01D 53/1493; C08J 11/02; Y02P 20/154
See application file for complete search history.

(56) References Cited

OTHER PUBLICATIONS

International Search Report for International Application No. PCT/US2015/059658, International Filing Date Nov. 9, 2015, dated Jan. 21, 2016, 5 pages.

Written Opinion for International Application No. PCT/US2015/059658, International Filing Date Nov. 9, 2015, dated Jan. 21, 2016, 6 pages.

* cited by examiner

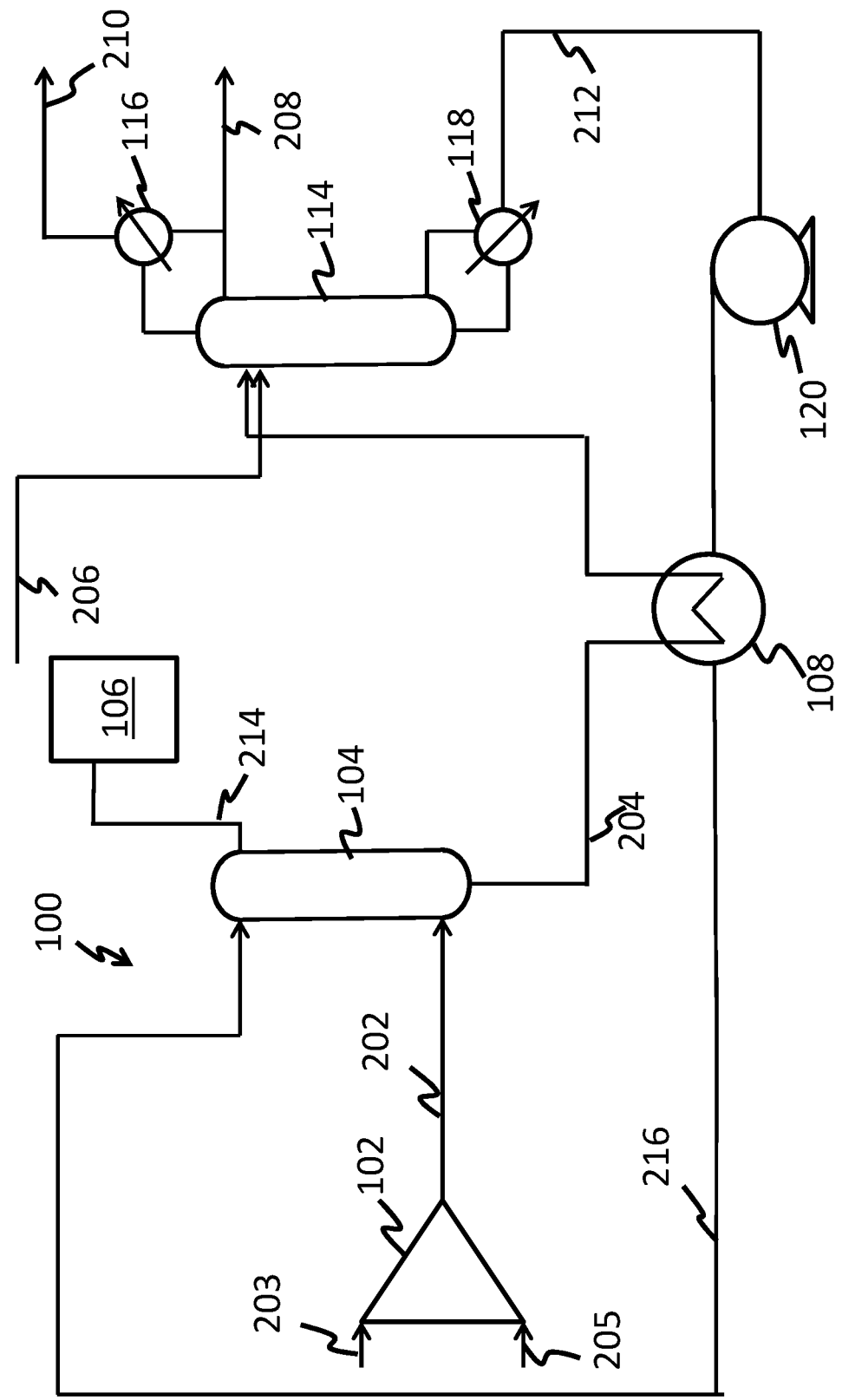

PROCESS FOR PURIFICATION OF VENT STREAMS

CROSS REFERENCE TO RELATED APPLICATIONS

This application is a National Stage application of PCT/US2015/059658, filed Nov. 9, 2015, which claims the benefit of U.S. Provisional Application No. 62/093,656, filed Dec. 18, 2014, both of which are incorporated by reference in their entirety herein.

BACKGROUND

This disclosure is related to a process for purification of a vent stream. In particular, this disclosure is related a process for removing halogenated compounds from polyolefin vent streams generated during the manufacturing of a polymer.

Catalysts are often used in the manufacturing of polymers especially polyolefins. Minor amounts of the catalyst used in the manufacture of polyolefins form multi-fluorinated by-products (e.g., pentafluoro-benzene (PFB) and other fluorinated benzene molecules) and other halogenated by-products (hereinafter collectively termed halogenated by-products) in small quantities. The by-products are contained in the vent stream that is discharged from the polyolefin manufacturing facility to control the rate of build-up of these products in the manufacturing process. These vent streams are most often sent to an adjacent hydrocarbon facility in order to collect and reprocess the valuable ethylene contained in the stream.

Even in small quantities, the presence of these halogenated by-products in the vent stream dictates that the vent streams are transported to the heavier hydrocarbon processing side of the process, where some of the halogenated materials are converted to hydrogen fluoride, which is highly corrosive. If these trace amounts of hydrogen fluoride are not removed from the vent stream, severe corrosion of the manufacturing facility can occur. The alternative is to incinerate (destroy) the vent stream and with it the valuable ethylene stream that can be salvaged.

It is therefore desirable to capture some of the halogenated by-products that are present in the vent stream thus reducing the level of halogenated species to an acceptable level while at the same time recovering ethylene contained in the stream and using it to manufacture additional polymer.

SUMMARY

Disclosed herein is a system for recovering olefins from a vent stream comprising an absorber; and a stripper; where the absorber and the stripper are in a recycle loop; and where the absorber is operative to treat a vent stream with a solvent to remove more than 99 wt % of a halogenated by-product contained in the vent stream and to recover 90 to 95 wt % of olefin molecules present in the vent stream; and where the stripper is operative to remove more than 99 wt % of the halogenated by-products present in the solvent; and where the solvent is recycled to the absorber.

Disclosed herein too is a method comprising charging a vent stream that comprises 90 to 95 wt % of olefin molecules, 5 to 7 wt % of alkanes and $1.0\times10^{-2}$ to $2\times10^{-2}$ wt % of a halogenated by-product, based on the total weight of the vent stream to an absorber; discharging from the absorber an olefin rich stream that comprises 90 to 95 wt % of olefin molecules, 5 to 7 wt % of alkanes and $1.0\times10^{-4}$ to $2\times10^{-4}$ wt % of the halogenated by-product, based on a total weight of the olefin rich stream; charging a stripper with a halogen concentrated stream received from the absorber; discharging from the stripper a solvent rich stream that is recycled to the absorber; and discharging from the stripper to an incinerator a waste stream that contains a substantial portion of the halogenated by-products present in the vent stream.

Disclosed herein too is a composition comprising an olefin rich stream that comprises 90 to 95 wt % of olefin molecules; 5 to 7 wt % of alkanes; and $1.0\times10^{-4}$ to $2\times10^{-4}$ wt % of the halogenated by-product, based on a total weight of the olefin rich stream.

BRIEF DESCRIPTION OF THE FIGURES

FIG. 1 depicts a schematic diagram of an exemplary single stage system 100 that is used for removing halogenated by-products from a vent stream while recycling usable olefin molecules to a polymer production facility for conversion to polymers.

DETAILED DESCRIPTION

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the FIGURE. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

The transition term "comprising" encompasses the transition terms "consisting of" and "consisting essentially of".

Various numerical ranges are disclosed herein. These ranges are inclusive of the endpoints as well as numerical values between these endpoints. The numbers in these ranges are interchangeable.

The term "line" as used herein refers to flow path between two points. The flow path may include a conduit, a pipe, a hose, or the like.

The term "and/or" includes both "and" as well as "or". For example "A and/or B" includes "A", "B", or "A and B".

Disclosed herein is a system for removing halogenated by-products from a vent stream obtained during the manufacture of polyolefins while at the same time recapturing olefin molecules contained in the vent stream for recycling. The system comprises an absorber/stripper combination that circulates the solvent from the process and provides a means for capturing the halogenated by-products and reducing the level of halogenated species to an acceptable level. This is accomplished by making use of a small portion of the solvent already used in the process to capture the halogenated materials and re-route the materials to a destruction device (e.g., an incinerator).

The system is advantageous in that converts an original vent stream comprising 90 to 95 wt %, preferably 91 to 93 wt % of olefin molecules, 5 to 7 wt % of alkanes and $1.0 \times 10^{-2}$ to $2 \times 10^{-2}$ wt % of the halogenated by-product (based on the total weight of the vent stream) to produce an olefin rich stream 214 that (is sent back to the polymer manufacturing facility) that comprises 90 to 95 wt %, preferably 91 to 93 wt % of olefin molecules, 5 to 7 wt % of alkanes and $1.0 \times 10^{-4}$ to $2 \times 10^{-4}$ wt % of the halogenated by-product (based on a total weight of the olefin rich stream). In short, the system 100 is operative to remove more than 99 wt % and preferably more than 99.9 wt % of the halogenated by-product that is present in the original vent stream.

Disclosed herein too is a method of purifying a vent stream that contains halogenated by-products obtained from a polymer manufacturing facility. The method comprises absorbing the halogenated by-products into a solvent and then stripping the solvent to remove the halogen by-products. During the absorption process in the absorber, olefins are separated from the vent stream and these are recycled to a manufacturing facility. The halogenated by-products that are stripped out are incinerated and destroyed.

The method described herein may be used in any type of polymerization process employing one or more monomers. Examples of monomers include unsaturated hydrocarbons having from 2 to 30 carbon atoms, preferably 2 to 12 carbon atoms, and more preferably 2 to 8 carbon atoms. Useful monomers include linear, branched or cyclic olefins; linear branched or cyclic alpha olefins; linear, branched or cyclic diolefins; linear branched or cyclic alpha-omega olefins; linear, branched or cyclic polyenes; linear branched or cyclic alpha olefins. Particularly preferred monomers include one or more of ethylene, propylene, butene-1, pentene-1,4-methyl-pentene-1, hexene-1, octene-1, decene-1,3-methyl-pentene-1, norbornene, norbornadiene, 3,5,5-trimethyl-1-hexene, 5-ethyl-1-nonene, vinyl norbornene, ethylidene norbornene monomers, or a combination thereof.

In an exemplary embodiment, the polymer produced herein is an ethylene homopolymer or copolymer. In another exemplary embodiment, the process relates to the polymerization of ethylene and one or more $C_4$ to $C_{20}$ linear, branched or cyclic monomers, preferably $C_4$ to $C_{12}$ linear or branched alpha-olefins. In a preferred embodiment, the comonomer comprises at least one comonomer having from 3 to 8 carbon atoms, preferably 4 to 8 carbon atoms. Particularly, the comonomers are propylene, butene-1,4-methyl-pentene-1,3-methyl-pentene-1, hexene-1 and octene-1, the most preferred being hexene-1, butene-1 and/or octene-1.

The solvent is selected to facilitate absorption of the halogenated by-products in the vent stream. The solvent is one that is capable of dissolving the olefin monomers to facilitate their removal from the vent stream. The solvent may be toluene, diesel, isoparaffinic fluids (such as for example ISOPAR™), normal paraffins (e.g., decane and dodecane) NORPAR™ or a combination thereof.

FIG. 1 depicts a schematic diagram of an exemplary single stage system 100 that is used for removing halogenated by-products from a vent stream while recycling usable olefin molecules to a polymer production facility for conversion to polymers. While the FIG. 1 depicts only a single stage, the system can employ a plurality of stages to effect the maximum removal of the halogenated by-product from the vent stream while at the same time effecting the maximum recovery of olefin molecules. In one embodiment, the number of stages can be 5 to 20, and preferably 10 to 12. The stages can be in series, parallel or in a combination of series and parallel.

The system 100 comprises an optional mixer 102 that receives a one or more vent streams (from a polymer manufacturing facility) that contains halogenated by-products and unused olefin molecules. The olefin molecules include unreacted monomers, as well as low molecular weight reacted species such as dimers, trimers, and the like, that generally have up to 5 repeat units. The halogenated by-products can include a variety of different halogenated molecules chief amongst which are pentafluoro-benzenes (PFBs). In one embodiment, a plurality of vent streams may be fed to the optional mixer 102 where they are mixed. The FIG. 1 depicts two vent streams 203 and 205 (from different manufacturing facilities) that are fed to the mixer 102. If a single vent stream is fed to the system 100, or alternatively, if a plurality of vent streams having substantially identical compositions are fed to the system 100, then the mixer 102 may be bypassed if desired.

The mixer 102 may simply be a container fitted with an agitation device in which the various streams are mixed. Alternatively, the mixer may simply be a container (with no agitation device) into which the contents of various streams are charged prior being discharged to an absorber 104.

The vent stream 202 is generally charged to the absorber 104 under pressure at values of 10 to 30 kilograms per square centimeters ($kg/cm^2$). The vent stream 202 comprises about 7- to 95 wt % of olefin molecules. It also contains alkanes such as, for example, methane and ethane, which increase pressure in the vent stream 202 and which need to be removed. The vent stream 202 also contains halogenated by-products in amounts of 0.50 (50 parts per million) to 2.5 wt % (250 parts per million) based on the total weight of the vent stream. It is these halogenated by-products that are to be removed so as to minimize corrosion and environmental damage.

The absorber 104 lies downstream of the mixer 102 and is in fluid communication with it. The absorber 104 receives a vent stream 202 from the mixer 102 and receives a stream of substantially pure recycled solvent 216 (hereinafter solvent stream 216). The solvent stream 216 contacts the vent stream 202 in the absorber 104 and absorbs the halogenated by-products from the vent stream. The molar solvent flow rate is set at 2 to 6 moles, preferably 3 to 5 moles of solvent for every 35 to 40 moles of incoming gas bearing the halogenated by-products (e.g., the fluorinated components).

In an embodiment, the solvent stream 216 enters the absorber 104 at the top of the device and is distributed across the vent stream 202 under pressure at a low temperature to preferentially absorb the halogenated by-products over the olefin molecules. The temperature and pressures in the absorber 104 are selected so as to facilitate absorption of greater than 90 wt %, preferably greater than 95 wt % and more preferably greater than 98 wt % of the halogenated by-products in the vent stream, based on the total weight of the halogenated by-products in the vent stream. In an exemplary embodiment, an amount of over 99 wt % of the halogenated by-products present in the vent stream are removed from the vent stream.

The pressure in the absorber 104 is lower than the pressure in the vent stream 202. The pressure in the absorber 104 varies from 10 to 30 $kg/cm^2$, preferably 11 to 20 $kg/cm^2$ and more preferably 12 to 18 $kg/cm^2$. The temperature in the absorber 102 is maintained at a value that facilitates the absorption of the halogenated by-products over the absorption of the olefin molecules. In an embodiment, the temperature in the absorber 102 is 15 to 60° C., preferably 25 to 55° C. and more preferably 35 to 50° C.

The remainder of the vent stream containing mostly polyolefins are then discharged from the absorber 104 via olefin rich stream 214 to a storage tank 106 from where they are fed to the manufacturing facility (not shown) for further processing. The olefin rich stream 214 contains less than 2 wt %, preferably less than or equal to 1 wt % of the halogenated by-products originally present in the vent stream 202.

The stream 204 (hereinafter the "halogen concentrated stream) emanating from the absorber 104 and containing a high concentration of the fluorinated by-product in addition to solvent is then charged to a stripper 114 via a heat exchanger 108. The heat exchanger 108 lies downstream of the absorber 104 and upstream of the stripper 114 and is in fluid communication with both of them.

The halogen concentrated stream 204 containing most of the halogenated by-products (and devoid of most of the olefins) present in the vent stream 202 is discharged from the absorber 104 to the heat exchanger 108 where it absorbs heat from a stream of substantially pure solvent 212 (hereinafter solvent rich stream 212) that is discharged from the stripper 114. As seen in the FIG. 1, the stripper 114 lies downstream of the absorber 104 and is in a recycle loop with it. In other words, some of the output of the absorber 104 is charged to the stripper 114, while some of the output of the stripper 114 is charged back to the absorber 104. In short, since the absorber 104 and the stripper 114 are in a recycle loop, each can be considered to be simultaneously upstream as well as downstream of the other.

The heat absorbed by the stream 204 makes the stripping process more efficient by facilitating the absorption of smaller amounts of heat in the stripper 114. The halogen concentrated stream 204 is then discharged from the heat exchanger 108 to the stripper 114. A make-up solvent stream 206 containing make-up solvent is also charged to the stripper 114. The make-up solvent is added to the stripper 114 to compensate for the slight loss of solvent that occurs during the stripping process.

The stripper 114 operates at a temperature and a pressure that is operative to remove the solvent from the halogen concentrated stream while leaving behind a halogen waste stream (a gaseous waste stream 210 and a liquid waste stream 208) that is concentrated with the halogen by-products. The solvent rich stream 212 containing less than 1 ppm of the halogenated by-product is then recycled from the stripper 114 to the absorber 104.

The stripper 114 is generally operated at a temperature that is greater than the boiling point of the solvent. As noted above, the solvent is selected to facilitate absorption of the halogenated by-products in the vent stream. The solvent is one that is capable of dissolving the olefin monomers to facilitate their removal from the vent stream. The stripper 114 operates at a pressure of 1 $kg/cm^2$ to 4 $kg/cm^2$, preferably at 1.5 $kg/cm^2$ to 2.5 $kg/cm^2$ and at a temperature of 75 to 250° C., preferably 100 to 200° C., and more preferably 135 to 155° C.

The halogen by-product stream comprises two streams—a gaseous stream 210 and a liquid stream 208 that are concentrated with the halogen by-product. These streams emanate from the stripper via a condenser 116 that serves to cool them. The gaseous stream 210 and the liquid stream 208 are eventually subjected to incineration and destroyed.

The solvent rich stream 212 containing less than 1 ppm of the halogen by-product is heated in a reboiler 118 and then recycled to the heat exchanger 108 (via a pump 120) where it exchanges its heat with the halogen concentrated stream 204 to become solvent stream 216 which is then recycled to the absorber 104. The pump 120 increases the pressure of the solvent rich stream 212 to a pressure that is greater than the operating pressure of the absorber 104. In an embodiment, the pressure of the solvent rich stream is increased to a pressure greater than 13 $kg/cm^2$, preferably greater than 15 $kg/cm^2$ and more preferably greater than 16 $kg/cm^2$. In an exemplary embodiment, the pressure of the solvent rich stream is increased to an amount of greater than or equal to 17 $kg/cm^2$.

The system disclosed herein is advantageous in that it reduces the amount of fluorinated material by an amount of greater than 99.9 wt % with the appropriate solvent flow rate and by using the appropriate number of contact stages.

The system and the method detailed herein are exemplified by the following non-limiting example.

EXAMPLE

This is a paper example that demonstrates the parameters and the efficiency of the system in removing halogenated by-products from an exemplary vent stream emanating from a polymer manufacturing facility. The system comprises a single stage which contains a single absorber and a single stripper. In short, the system is similar to that shown in the FIG. 1 and the numerals used to represent stream numbers are similar to those employed in the FIG. 1. Table 1 show the flow rates in the various streams along with the pressure and the temperature of each stream in the system of FIG. 1.

TABLE 1

| Stream No. (mass flow rate) | Vent stream 202 (kg/hr) | Olefin rich stream 214 (kg/hr) | Gaseous stream 210 (kg/hr) | Liquid stream 208 (kr/hr) | Make-up solvent stream 206 (kg/hr) |
|---|---|---|---|---|---|
| Total Flow (kmol/hr) | 38.61 | 37.87 | 0.73 | 0.84 | 0.847 |
| Total Flow (kg/hr) | 1050 | 1032.37 | 26.09 | 80.19 | 88.660 |
| Total Flow (m³/hr) | 53.21 | 66.73 | 9.44 | 0.12 | 0.130 |
| Temperature ° C. | 44.98 | 44.71 | 40 | 40 | 40 |
| Pressure (bar) | 17.6 | 14.01 | 2 | 2 | 20 |

From the Table 1 above it may be seen that the pressure in the vent stream is greater than that in the olefin rich stream (and consequently greater than the pressure in the absorber). It also shows that the temperature in the vent stream is almost the same as the temperature in the olefin rich stream (and consequently in the absorber). A small amount of make-up solvent of 1 to 5 wt % of the total weight of the vent stream is added is added during each recycle step. In an exemplary embodiment, about 2 wt % of solvent (based on the total weight of the vent stream 202) is added during to the system during each cycle.

The chemical make-up of each of the streams in the system 100 is shown below in the Table 2.

TABLE 2

| Stream No. (mass flow rate) | Vent stream 202 (kg/hr) | Olefin rich stream 214 (kg/hr) | Gaseous stream 210 (kg/hr) | Liquid stream 208 (kr/hr) | Make-up solvent stream 206 (kg/hr) |
|---|---|---|---|---|---|
| Hydrogen | 2.46 | 2.46 | 0.0024 | 3.96E−06 | 0 |
| Nitrogen | 2.60 | 2.59 | 0.010 | 3.22E−05 | 0.0049 |
| Methane | 34.46 | 34.240 | 0.22 | 0.002 | 0.00047 |
| Ethylene (olefin molecule) | 943.64 | 926.25 | 16.78 | 0.650 | 0.0429 |
| Ethane | 34.56 | 33.55 | 0.96 | 0.0580 | 0.0044 |
| PFB (halogenated by-product) | 0.157 | 0.0015 | 0.022 | 0.146 | 0.0132 |

From the Table 2 it may be seen that the percentage of the halogenated by-product in the original vent stream 202 is less than 0.0157 wt %. Most of the halogenate by-product is removed by the system 100 and is present in the gaseous stream 210 and the liquid stream 208, both of which are incinerated. More than 98 wt % of the olefin present in the original vent stream is recovered and sent back to the polymer manufacturing facility for conversion to a polymer.

From the Table 2 it may be seen that the original vent stream 202 comprises 90 to 95 wt %, preferably 91 to 93 wt % of olefin molecules, 5 to 7 wt % of alkanes and $1.0 \times 10^{-2}$ to $2 \times 10^{-2}$ wt % of the halogenated by-product, based on the total weight of the vent stream. The vent stream 202 is treated by the system 100 to produce the olefin rich stream 214 (that is sent back to the polymer manufacturing facility) has a composition that comprises 90 to 95 wt %, preferably 91 to 93 wt % of olefin molecules, 5 to 7 wt % of alkanes and $1.0 \times 10^{-4}$ to $2 \times 10^{-4}$ wt % of the halogenated by-product, based on the total weight of the olefin rich stream. In short, the system 100 is operative to remove more than 99 wt % and preferably more than 99.9 wt % of the halogenated by-product that is present in the original vent stream 202.

What is claimed is:

1. A system for recovering olefins from a vent stream comprising:
   a mixer that is operative to receive a plurality of vent streams that contain halogenated by-products and to mix the respective vent streams;
   an absorber located downstream of the mixer and in fluid communication with the mixer; and
   a stripper; where the absorber and the stripper are in a recycle loop; and where the absorber is operative to treat a vent stream with a solvent to remove more than 99 wt % of a halogenated by-product contained in the vent stream and to recover 90 to 95 wt % of olefin molecules present in the vent stream; and where the stripper is operative to remove more than 99 wt % of the halogenated by-products present in the solvent; and where the solvent is recycled to the absorber.

2. The system of claim 1, further comprising a heat exchanger that lies downstream of the absorber and upstream of the stripper; where the heat exchanger is operative to transfer heat from a halogen concentrated stream discharged from the absorber to a solvent rich stream discharged from the stripper.

3. The system of claim 1, where the absorber functions at a lower pressure than a pressure in the vent stream.

4. The system of claim 1, further comprising a condenser and a reboiler, where the condenser and the reboiler are located downstream of the stripper and are operative to discharge a liquid stream and a gaseous stream respectively to an incinerator; where the liquid stream and the gaseous stream together contain a substantial portion of the halogenated by-products present in the vent stream.

5. The system of claim 1, where the system is operative to convert the vent stream comprising 90 to 95 wt % of olefin molecules, 5 to 7 wt % of alkanes and $1.0 \times 10^{-2}$ to $2 \times 10^{-2}$ wt % of the halogenated by-product, based on the total weight of the vent stream, to produce an olefin rich stream 214 that comprises 90 to 95 wt % of olefin molecules, 5 to 7 wt % of alkanes and $1.0 \times 10^{-4}$ to $2 \times 10^{-4}$ wt % of the halogenated by-product, based on a total weight of the olefin rich stream.

6. The system of claim 1, where the olefin molecule comprises ethylene and where the halogenated by-product is pentafluoro-benzene.

7. The system of claim 1, where the solvent comprises toluene, diesel, isoparaffinic solvents or a combination thereof.

* * * * *